United States Patent
Han et al.

(10) Patent No.: US 11,248,170 B2
(45) Date of Patent: Feb. 15, 2022

(54) POLYMERIZABLE COMPOUND AND APPLICATION THEREOF

(71) Applicant: Jiangsu Hecheng Display Technology Co., Ltd., Yangzhong (CN)

(72) Inventors: Wenming Han, Yangzhong (CN); Wenyang Ma, Yangzhong (CN); Shuang Xu, Yangzhong (CN); Haibin Xu, Yangzhong (CN)

(73) Assignee: Jiangsu Hecheng Display Technology Co., Ltd., Yangzhong (CN)

( * ) Notice: Subject to any disclaimer, the term of this patent is extended or adjusted under 35 U.S.C. 154(b) by 43 days.

(21) Appl. No.: 16/499,969

(22) PCT Filed: Apr. 20, 2018

(86) PCT No.: PCT/CN2018/083866
§ 371 (c)(1),
(2) Date: Oct. 1, 2019

(87) PCT Pub. No.: WO2018/192565
PCT Pub. Date: Oct. 25, 2018

(65) Prior Publication Data
US 2020/0339883 A1    Oct. 29, 2020

(30) Foreign Application Priority Data

Apr. 21, 2017    (CN) .......................... 201710266313.5

(51) Int. Cl.
| | |
|---|---|
| G02F 1/1333 | (2006.01) |
| C09K 19/14 | (2006.01) |
| C09K 19/20 | (2006.01) |
| C09K 19/30 | (2006.01) |
| C09K 19/38 | (2006.01) |

(52) U.S. Cl.
CPC .............. C09K 19/14 (2013.01); C09K 19/20 (2013.01); C09K 19/3028 (2013.01); C09K 19/3066 (2013.01); C09K 19/3809 (2013.01)

(58) Field of Classification Search
CPC .... C09K 19/3809; C09K 19/14; C09K 19/20; C09K 19/3028; C09K 19/3066; G02F 1/1333
USPC .................................................... 252/299.66
See application file for complete search history.

(56) References Cited

U.S. PATENT DOCUMENTS

| | | | |
|---|---|---|---|
| 6,090,308 | A | 7/2000 | Coates et al. |
| 6,136,225 | A | 10/2000 | Meyer et al. |
| 7,919,009 | B2 | 4/2011 | Itano et al. |
| 8,425,800 | B2 | 4/2013 | Hirata et al. |
| 8,895,117 | B2 | 11/2014 | Jansen et al. |
| 9,725,651 | B2 | 8/2017 | Hirata et al. |
| 2008/0303001 | A1 | 12/2008 | Hattori et al. |
| 2011/0253933 | A1 | 10/2011 | Hirata et al. |
| 2013/0334462 | A1 | 12/2013 | Sudo et al. |
| 2014/0132899 | A1* | 5/2014 | Hsieh ................ G02F 1/133711 349/106 |
| 2015/0299570 | A1* | 10/2015 | Kurisawa ........... C09K 19/3001 252/299.61 |
| 2015/0368558 | A1 | 12/2015 | Song et al. |
| 2015/0376505 | A1 | 12/2015 | Gotoh et al. |
| 2016/0122650 | A1* | 5/2016 | Hirata ................ C09K 19/2014 252/299.4 |
| 2020/0339883 | A1* | 10/2020 | Han ....................... C09K 19/14 |

FOREIGN PATENT DOCUMENTS

| | | |
|---|---|---|
| CN | 1173891 A | 2/1998 |
| CN | 101568559 A | 10/2009 |
| CN | 101671252 A | 3/2010 |
| CN | 101679867 A | 3/2010 |
| CN | 102241988 A | 11/2011 |
| CN | 102964253 A | 3/2013 |
| CN | 103113900 A | 5/2013 |
| CN | 103180410 A | 6/2013 |
| CN | 104557545 A | 4/2015 |
| JP | 2003-193053 A | 7/2003 |
| JP | 2008239913 A | 10/2008 |

(Continued)

*Primary Examiner* — Geraldina Visconti
(74) *Attorney, Agent, or Firm* — Hoffmann & Baron, LLP

(57) ABSTRACT

The present invention provides a polymerizable compound with a structure of general formula I, which exhibits none or few of the problems existing in the prior art. A polymerizable liquid crystal composition comprising the polymerizable compound has good stability and higher reliability, and is embodied by having a smaller pretilt angle change and higher voltage holding ratio. Also, there is little or no image sticking effect in a liquid crystal display device comprising the polymerizable liquid crystal composition. The present invention also provides a method of synthesizing a polymerizable compound with a structure of general formula I. The present invention further provides a polymerizable liquid crystal composition comprising the polymerizable compound and a liquid crystal display device comprising the polymerizable liquid crystal composition.

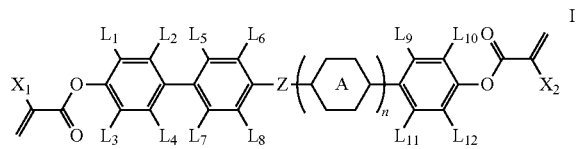

9 Claims, No Drawings

(56) References Cited

FOREIGN PATENT DOCUMENTS

| | | | |
|---|---|---|---|
| JP | 2011227187 A | 11/2011 | |
| JP | 20121623 A | 1/2012 | |
| JP | 201218215 A | 1/2012 | |
| JP | 201282351 A | 4/2012 | |
| JP | 2016-11346 A | 1/2016 | |
| KR | 20150139430 A | 12/2015 | |
| TW | 201544580 A | 12/2015 | |
| WO | 2013161669 A1 | 10/2013 | |
| WO | 2014148472 A1 | 9/2014 | |
| WO | 2015/182926 A1 | 3/2015 | |
| WO | 20150984493 A1 | 7/2015 | |
| WO | WO 2015182926 A1 * | 12/2015 | ........... G02F 1/1333 |

* cited by examiner

POLYMERIZABLE COMPOUND AND APPLICATION THEREOF

CROSS-REFERENCE TO RELATED APPLICATIONS

This application is the National Stage of International Application No. PCT/CN2018/083866, filed Apr. 20, 2018, which claims the benefit of Chinese Application No. 201710266313.5, filed Apr. 21, 2017, the contents of which is incorporated by reference herein.

TECHNICAL FIELD

The present invention relates to a polymerizable compound, in particular to a polymerizable compound having good stability and higher reliability and uses thereof.

BACKGROUND ARTS

Liquid crystal display elements can be used in various electrical apparatuses for domestic use, measuring apparatuses, automotive panels, word processors, computers, printers, televisions and so forth, such as clocks and calculators. Based on the types of display mode, liquid crystal display elements can be classified into PC (phase change), TN (twisted nematic), STN (super twisted nematic), ECB (electrically controlled birefringence), OCB (optically compensated bend), IPS (in-plane switching), VA (vertical alignment), CSH (color super homeotropic) and so forth. Based on the driving modes of elements, liquid crystal display elements can be classified into PM (passive matrix) type and AM (active matrix) type. PM is classified into static type, multiplex type and so forth. AM is classified into TFT (thin film transistor) type, MIM (metal insulator metal) type and so forth. The types of TFT comprise amorphous silicon and polycrystal silicon. The latter is classified into a high-temperature type and a low-temperature type according to the manufacturing process. Based on the types of light source, liquid crystal display elements are classified into a reflection type utilizing a natural light, a transmission type utilizing a backlight, and a semi-transmission type utilizing both the natural light and the backlight.

Among these display modes, IPS mode, ECB mode, VA mode, CSH mode or the like differ from the commonly used TN mode or STN mode in that the former uses a liquid crystal material having negative dielectric anisotropy. Among these display modes, there are applications of VA mode driven by AM in display elements requiring high speed and wide viewing angle, wherein the application in a liquid crystal element such as a television is most desirable.

The VA mode and IPS mode are both in normal black mode but different in that: liquid crystal molecules in the liquid crystal layer of the panel in VA mode are negative liquid crystal, and the transparent electrodes are disposed on the upper and lower substrates to form an electric field perpendicular to the substrates. When no voltage is applied, the long axis of liquid crystal molecules is perpendicular to the substrates, thereby forming a dark state; when a voltage is applied, the long axis of liquid crystal molecules falls down in a direction parallel to the substrates. The initial alignment also requires friction on the substrates, resulting in problems such as contamination, static electricity, and difficulty in controlling the pretilt angle. In order to solve problems in the initial alignment of the VA mode, there are various derivative modes, such as Multi-domain Vertical Alignment (MVA), Pattern Vertical Alignment (PVA), Polymer Sustained Alignment (PSA) and Polymer Stabilized Vertical Alignment (PSVA), wherein the PSA mode and PSVA mode have gradually predominated due to their characteristics such as high transmittance, high contrast and fast response.

The Polymer Sustained Alignment (PSA) type liquid crystal display device has a polymer structure formed in the cell so as to control the pretilt angles of liquid crystal molecules. It is applied as a liquid crystal display element due to its characteristics of fast response and high contrast.

The PSA type liquid crystal display element is manufactured as follows:

A polymerizable composition composed of liquid crystal compounds and polymerizable compounds is filled between the substrates, and a voltage is applied. The liquid crystal molecules are aligned, and the polymerizable compounds are polymerized to fix the orientation of the liquid crystal molecules. It is known that the display failure (i.e., image sticking) of the PSA type liquid crystal display element is caused by impurities and changes in orientation of liquid crystal molecules (changes in pretilt angle).

The reason why changes in the pretilt angle of molecules cause image sticking is that, when constituting an element, continuous display of same patterns for a long period of time causes changes in the structure of polymers, resulting in the change of pretilt angles thereof. Therefore, there is a need for a polymerizable compound which can form a polymer having an unchanged rigid structure.

PSVA uses polymerizable compounds to control the alignment direction of liquid crystal molecules: making the liquid crystals in a desirable alignment state via external electric field, keeping in such a state and exposing to UV to polymerize the polymerizable compounds in the liquid crystal mixture, thereby "solidifying" the desirable alignment state of the liquid crystals.

Since a rubbing alignment process is not required in PSVA mode, it is possible to avoid problems such as static electricity, contamination and so forth caused by friction in modes such as TN, IPS and so forth.

Unfortunately, there still are various defects in current polymerizable liquid crystal monomers. For example, the polymerizable liquid crystal monomer described in U.S. Pat. No. 6,136,225 has an exorbitant melting point and needs to be operated at a temperature of 80-90° C. in actual production, which results in large increase of energy consumption and being liable to cause defects that seriously affect optical quality, such as uneven alignment, abnormal polymerization, etc., at high temperatures.

Therefore, attempts have been made to improve the performance of polymerizable liquid crystals by methods of preparing polymerizable liquid crystal compositions. A polymerizable liquid crystal composition with a lower melting point is provided in Japanese Patent JP2003193053, whereas there is a problem of severely uneven alignment. A polymerizable liquid crystal composition with a lower melting point is provided in U.S. Pat. No. 6,090,308, whereas there are problems such as poor stability and easy crystallization at low temperatures.

A single polymerizable compound is generally used in the prior art, resulting in a variety of problems, for example: slower or faster polymerization, difficulty in control, larger change in pretilt angle, excessive residual amount after polymerization, poor UV stability, various display failures (such as residual image, uneven display), etc.

Therefore, there is a great need for a novel polymerizable liquid crystal composition which does not have or largely reduces the above disadvantages.

SUMMARY OF THE INVENTION

Objects: It is an object of the present invention to provide a polymerizable compound which exhibits none or few of the problems existing in the prior art. A polymerizable liquid crystal composition comprising the polymerizable compound has good stability and higher reliability, and is embodied by having a smaller pretilt angle change and higher voltage holding ratio. Also, there is little or no image sticking effect in a liquid crystal display device comprising the polymerizable liquid crystal composition.

Another object of the present invention is to provide a method of synthesizing the polymerizable compound.

A further object of the present invention is to provide a polymerizable liquid crystal composition comprising the polymerizable compound and a liquid crystal display device comprising the polymerizable liquid crystal composition.

Technical solutions: in order to achieve the above objects, the present invention provides a polymerizable compound having a structure of general formula I:

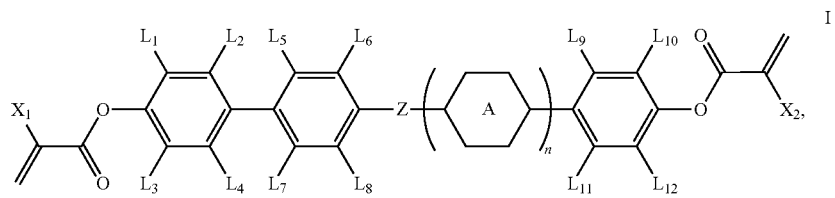

in which, $X_1$ and $X_2$ are same or different and each independently represents —H or —$CH_3$;

$L_1$-$L_{12}$ are same or different and each independently represents —H, —F or —$CH_3$;

Z represents —$CH_2O$—, —$OCH_2$—, —$CH_2CH_2$—, —COO—, —OCO—, —$CF_2O$— or —$OCF_2$—;

ring A represents

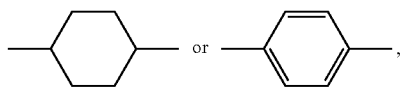

wherein one or more —$CH_2$— in ring

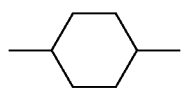

can be replaced by —O— or —N—; one or more —H on ring

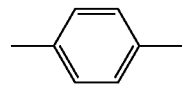

can be substituted by —F or —$CH_3$;

n represents 0 or 1.

In some embodiments of the present invention, the compound of general formula I is one or more compounds selected from compounds of general formulas I-1~I-3:

I-1

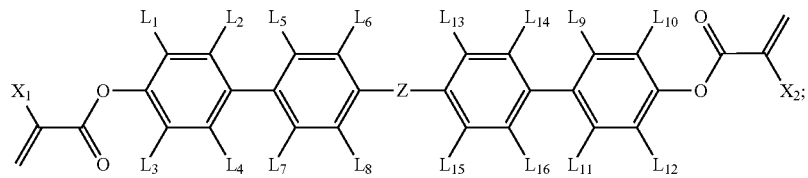

-continued

I-2

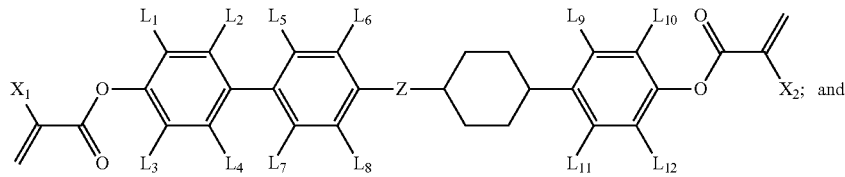

I-3

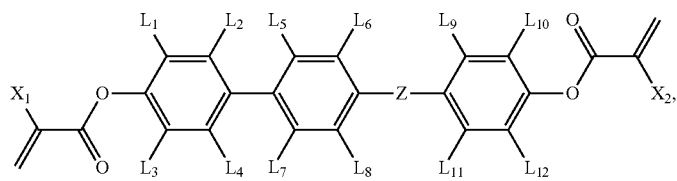

in which, $X_1$ and $X_2$ are same or different and each independently represents —H or —CH$_3$;

$L_1$-$L_{16}$ are same or different and each independently represents —H, —F or —CH$_3$;

Z represents —CH$_2$O—, —OCH$_2$—, —CH$_2$CH$_2$—, —COO—, —CF$_2$O— or —OCF$_2$—.

In some embodiments of the present invention, at least one of $L_1$-$L_{16}$ is —F or —CH$_3$.

In some embodiments of the present invention, Z represents —CH$_2$O—, —OCH$_2$—, —CH$_2$CH$_2$—, —COO— or —OCO—.

In some embodiments of the present invention, at least one of $L_5$-$L_8$ and/or $L_{13}$-$L_{16}$ in general formula I-1 is —F or —CH$_3$.

In some embodiments of the present invention, at least two of $L_1$-$L_{16}$ in general formulas I-1 and I-2 are —F or —CH$_3$.

In some embodiments of the present invention, Z represents —CH$_2$O—, —OCH$_2$— or —CH$_2$CH$_2$—.

In some embodiments of the present invention, the compound of general formula I-1 is one or more compounds selected from the following compounds:

I-1-1

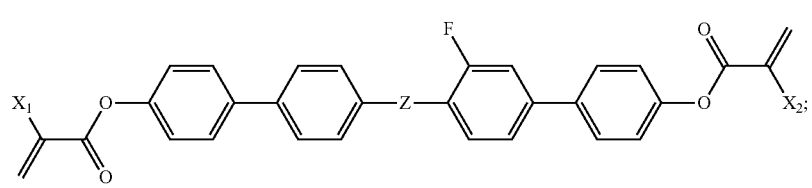

I-1-2

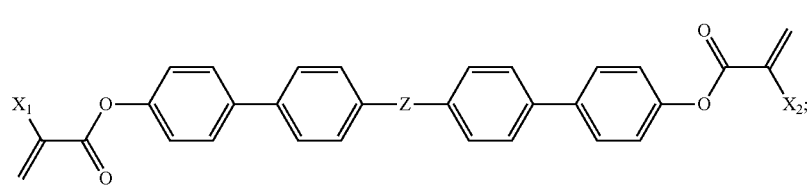

I-1-3

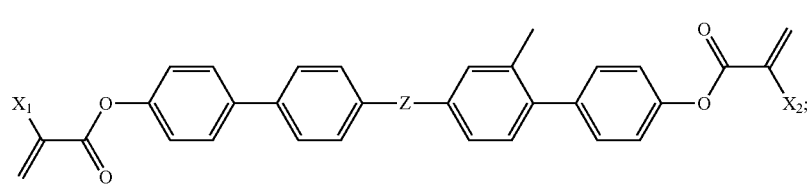

I-1-4

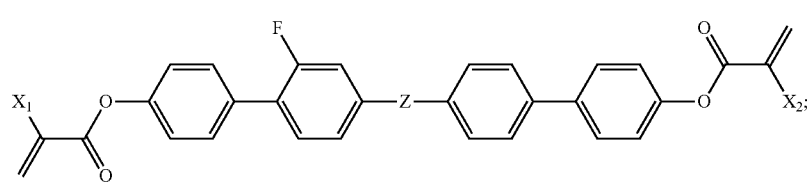

I-1-5
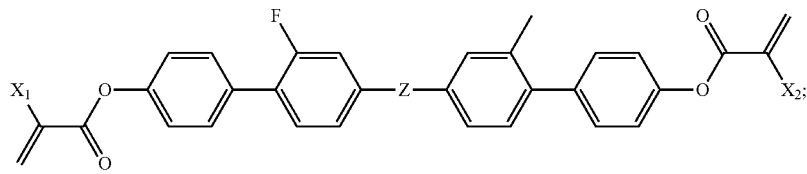
I-1-6
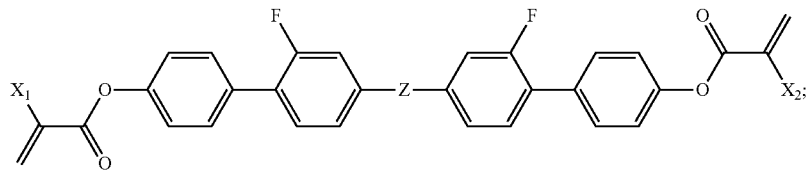
I-1-7
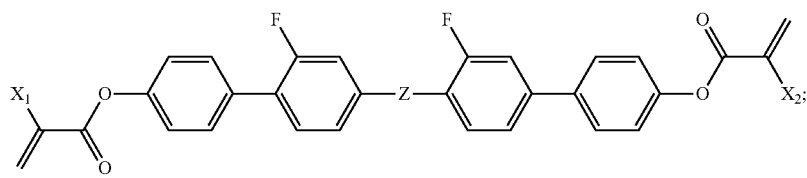
I-1-8
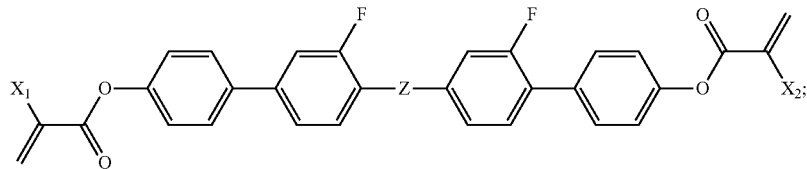
I-1-9
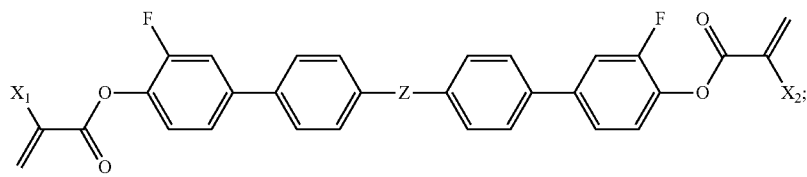
I-1-10
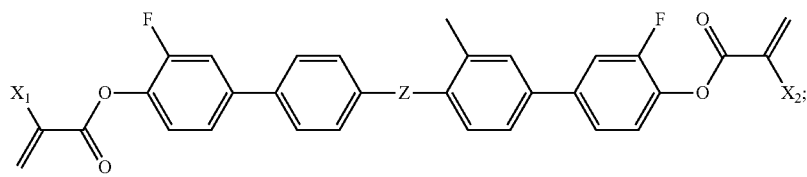
I-1-11
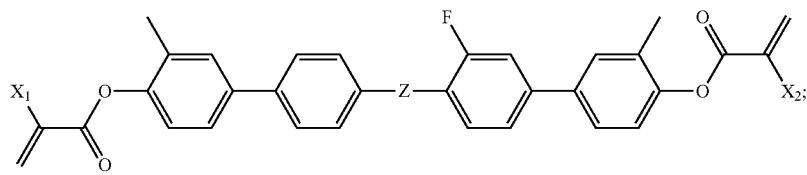
I-1-12
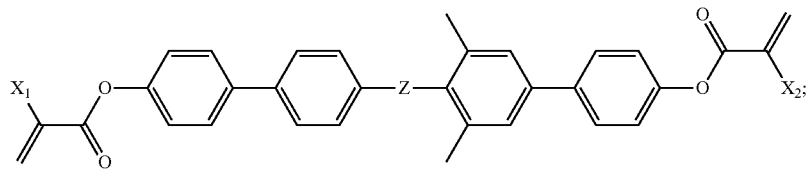

I-1-13
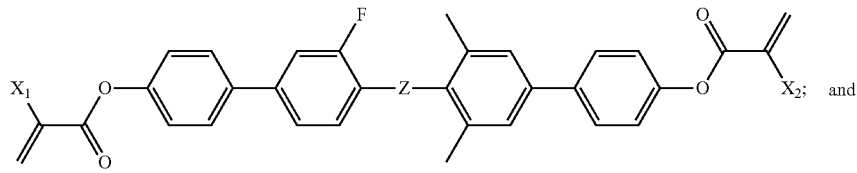
and
I-1-14
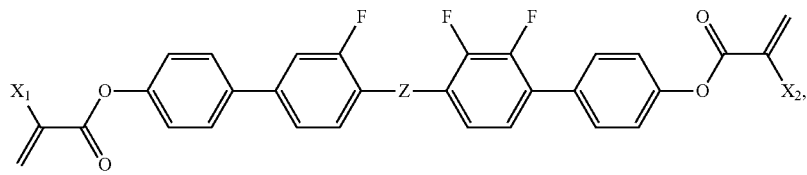
in which,
X₁ and X₂ are same or different and each independently represents —H or —CH₃;
Z represents —CH₂O—, —OCH₂— or —CH₂CH₂—.
In some embodiments of the present invention, the compound of general formula I-2 is one or more compounds selected from the following compounds:
I-2-1
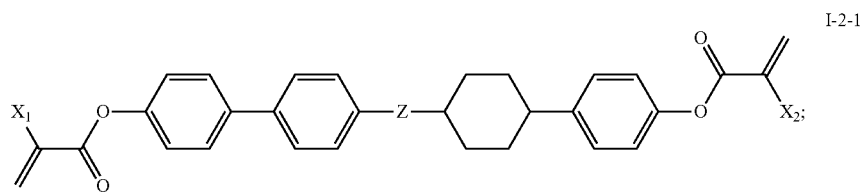
I-2-2
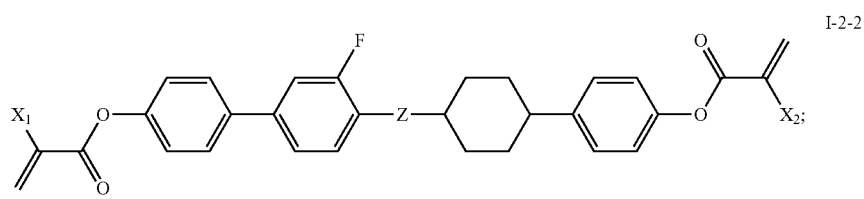
I-2-3
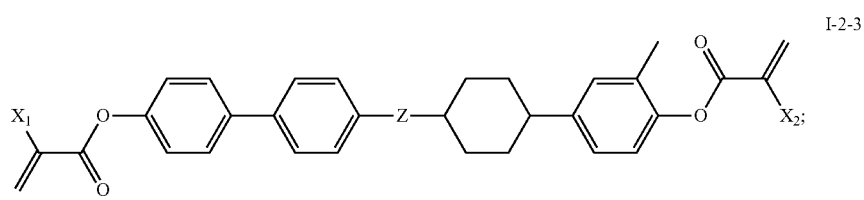
I-2-4
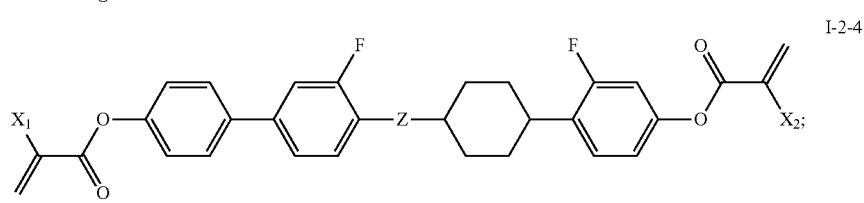
I-2-5
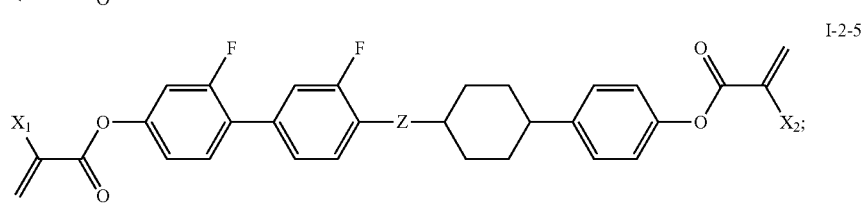

-continued

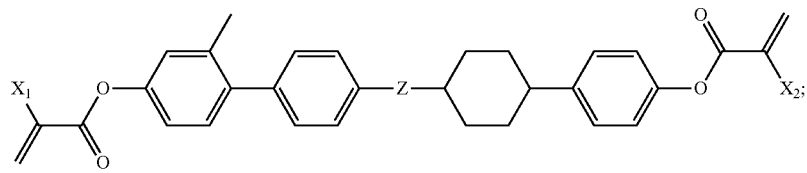
I-2-6 in which, $X_1$ and $X_2$ are same or different and each independently represents —H or —CH$_3$.

In some embodiments of the present invention, the compound of general formula I-3 is one or more compounds selected from the following compounds:

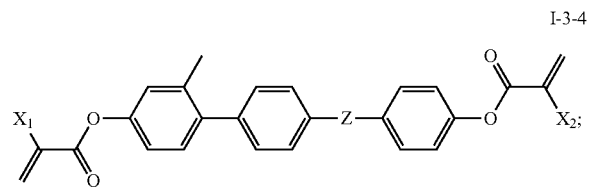
I-3-1

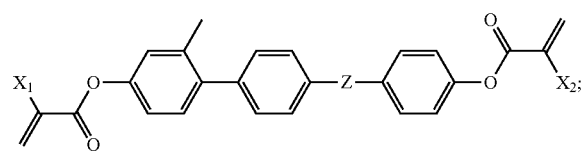
I-3-2

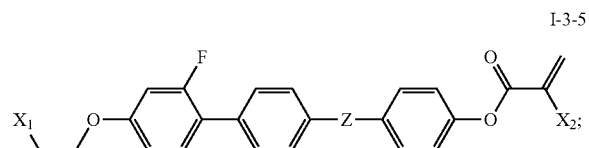
I-3-3

I-3-4

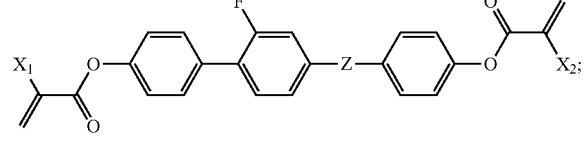
I-3-5

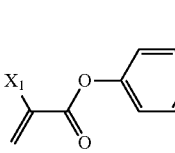
I-3-6

-continued

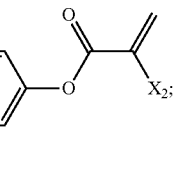
I-3-7

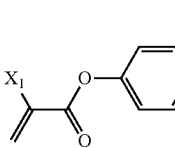
I-3-8

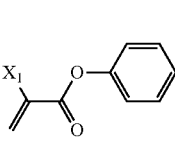
I-3-9 and

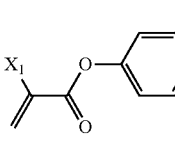
I-3-10 in which, $X_1$ and $X_2$ are same or different and each independently represents —H or —CH$_3$;

Z represents —CH$_2$O—, —OCH$_2$— or —CH$_2$CH$_2$—.

In another aspect, the present invention provides a polymerizable liquid crystal composition comprising the polymerizable compound with a structure of general formula I of the present invention.

In some embodiments of the present invention, the polymerizable liquid crystal composition comprises at least one compound selected from a group consisting of general formula I-1, general formula I-2 and/or general formula I-3.

In some embodiments of the present invention, the group consisting of general formula I-1, general formula I-2 and/or general formula I-3 provides 0.001 wt %-5 wt % of the polymerizable liquid crystal composition.

In still another aspect, the present invention provides a liquid crystal display device comprising the polymerizable liquid crystal composition of the present invention.

In yet another aspect, the present invention provides uses of the polymerizable liquid crystal composition of the present invention in PSVA and PVA display modes.

Beneficial effects: As compared to other polymerizable compounds in the prior art, the polymerizable compound with a structure of general formula I provided by the present invention exhibits none or few of the problems existing in the prior art. A polymerizable liquid crystal composition comprising the polymerizable compound has good stability and higher reliability, and is embodied by having a smaller pretilt angle change and higher voltage holding ratio. There is also little or no image sticking effect in a liquid crystal display device comprising the polymerizable liquid crystal composition. The preparation of the polymerizable compound with a structure of general formula I of the present invention has advantages of easily available raw materials, a simple and practicable synthesis route, and being suitable for large-scale industrial production.

DETAILED EMBODIMENTS

The present invention will be illustrated by combining the detailed embodiments below. It should be noted that, the following examples are exemplary embodiments of the present invention, which are only used to illustrate the present invention, not to limit it. Other combinations and various modifications within the conception of the present invention are possible without departing from the subject matter and scope of the present invention.

The abbreviated codes of the test items in the following Examples are as follows:

Y1: pretilt angle 1, the pretilt angle data tested after irradiation of test cell with UV lamp 1 for 3 minutes;

Y2: pretilt angle 2, the pretilt angle data tested after irradiation of test cell with UV lamp 1 for 3 minutes and the subsequent continuous illuminating of test cell with alternating current (16 V, 60 Hz) for 24 hours;

Y: the amount of pretilt angle change=pretilt angle 2−pretilt angle 1;

VHR1: the data of voltage holding ratio tested after irradiation of test cell with UV lamp 2 for 20 minutes;

VHR2: the data of voltage holding ratio tested after irradiation of test cell with UV lamp 1 for 3 minutes and the subsequent irradiation of test cell with UV lamp 2 for 60 minutes;

In which, the pretilt angle refers to the angle at which the alignment of the liquid crystal offsets by 90° (the initial pretilt angle of the vertically aligned test cell for testing is 1°);

The light intensity of UV lamp 1 is 50 mw/cm$^2$;

The light intensity of UV lamp 2 is 5 mw/cm$^2$.

The polymerizable compounds with the structure of general formula I prepared by the following Examples are tested for pretilt angle and voltage holding ratio according to the following methods:

selecting the commercial liquid crystal with No. HCMM-02 produced by Jiangsu Hecheng Display Technology Co., Ltd. as a host, dissolving the polymerizable compound with the structure of general formula I in the host liquid crystal in a percent of 0.1 wt %-0.3 wt %, and testing the polymerizable liquid crystal composition for pretilt angle and voltage holding ratio.

Example 1

The synthetic route of compound I-1-1-1 is shown as follows:

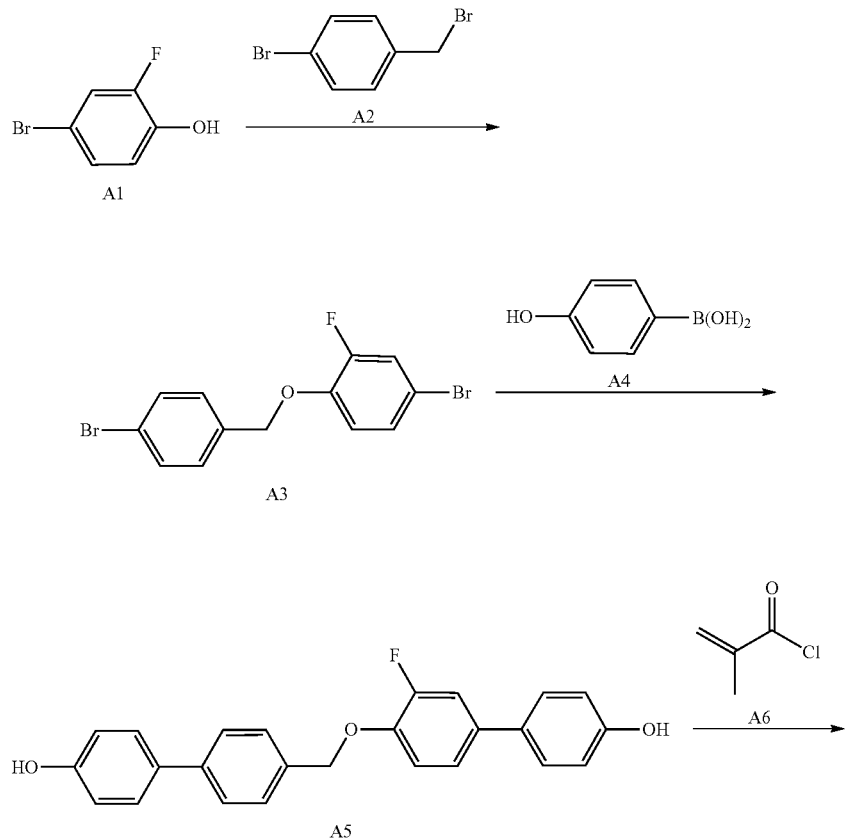

-continued

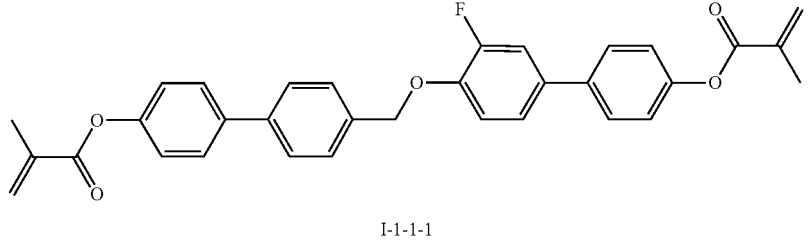

I-1-1-1

1) Synthesis of Compound A3

To a 500 ml three-necked flask was added 19.1 g A1, 200 ml ethanol, and 10 g sodium hydroxide. 25 g A2 was added in portions (5 g, 8 g, 12 g, in three portions) with stirring. The reaction mixture was heated to reflux for 3 hours. After post-treatment, 33 g compound A3 was obtained, GC>97%, yield: 92%.

2) Synthesis of Compound A5

To a 500 ml three-necked flask was added 18 g compound A3, 14 g A4, 21.2 g anhydrous sodium carbonate, 150 ml toluene, 75 ml ethanol, and 75 ml water. 0.5 g tetrakis(triphenylphosphine)palladium was added under nitrogen, and the reaction mixture was heated to reflux for 6 hours. After post-treatment, 5.2 g compound A5 was obtained, HPLC>95%, yield: 27%.

3) Synthesis of Compound I-1-1-1

To a 500 ml three-necked flask was added 2 g compound A5, 150 ml toluene, 50 ml triethylamine, and a trace amount of 2,6-di-tert-butyl-p-cresol. 1.2 g A6 was added dropwise under nitrogen. After the addition was completed, the reaction mixture was stirred for 6 hours at a controlled temperature of 40° C. After post-treatment, 1 g compound I-1-1-1 was obtained, HPLC>99%, yield: 38%.

The mass spectrum data of compound I-1-1-1 is as follows:

Ms: 522 (2.8%) 251 (100%) 69 (45%).

According to the above synthesis methods, target compounds can be obtained by substituting the compounds shown in Table 1 for compounds A1, A2, A4 and A6:

TABLE 1

| Alternative compound of A1 | Alternative compound of A2 | Alternative compound of A4 | Alternative compound of A6 | Target compound |
|---|---|---|---|---|
| 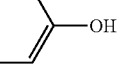 | 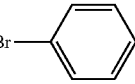 | 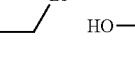 | 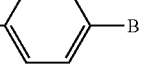 | I-1-2-1 |
| 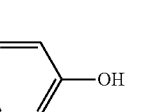 | 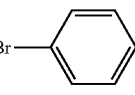 | 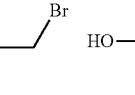 | 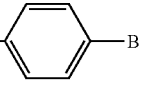 | I-1-3-1 |
| 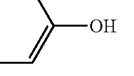 | 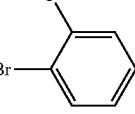 | 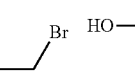 | 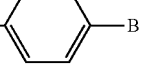 | I-1-4-1 |
| 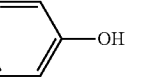 | 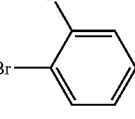 | 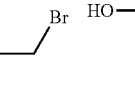 | 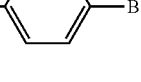 | I-1-5-1 |
| 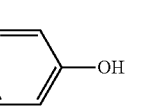 | 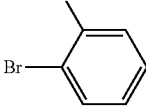 | 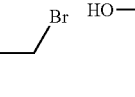 | 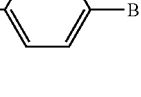 | I-1-6-1 |
| 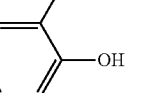 | 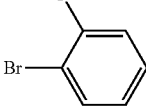 | 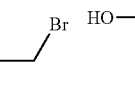 | 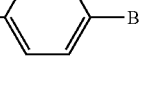 | I-1-7-1 |

TABLE 1-continued

| Alternative compound of A1 | Alternative compound of A2 | Alternative compound of A4 | Alternative compound of A6 | Target compound |
|---|---|---|---|---|
| 4-bromo-3-fluorophenol | 4-bromo-2-fluorobenzyl bromide | 4-hydroxyphenylboronic acid | methacryloyl chloride | I-1-8-1 |
| 4-bromophenol | 4-bromobenzyl bromide | 3-fluoro-4-hydroxyphenylboronic acid | methacryloyl chloride | I-1-9-1 |
| 4-bromo-2-methylphenol | 4-bromobenzyl bromide | 2-fluoro-4-hydroxyphenylboronic acid | methacryloyl chloride | I-1-10-1 |
| 4-bromo-2-fluorophenol | 4-bromobenzyl bromide | 4-hydroxy-3-methylphenylboronic acid | methacryloyl chloride | I-1-11-1 |
| 4-bromo-2,6-dimethylphenol | 4-bromobenzyl bromide | 4-hydroxyphenylboronic acid | methacryloyl chloride | I-1-12-1 |
| 4-bromo-2,6-dimethylphenol | 4-bromo-2-fluorobenzyl bromide | 4-hydroxyphenylboronic acid | methacryloyl chloride | I-1-13-1 |
| 4-bromo-2,3-difluorophenol | 4-bromo-2-fluorobenzyl bromide | 4-hydroxyphenylboronic acid | methacryloyl chloride | I-1-14-1 |

The specific structures of the target compounds in Table 1 are shown as follows:

I-1-2-1

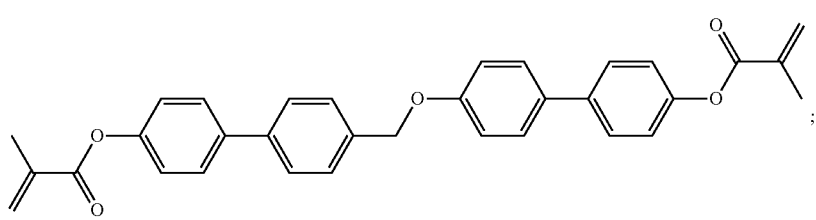

;

-continued
I-1-3-1
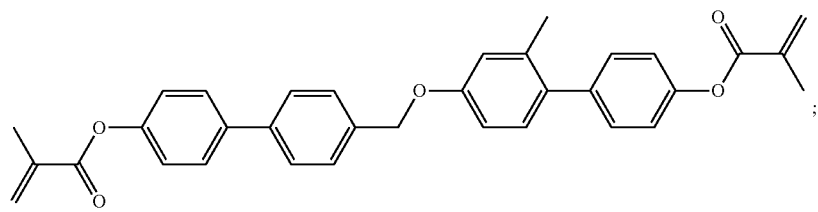
I-1-4-1
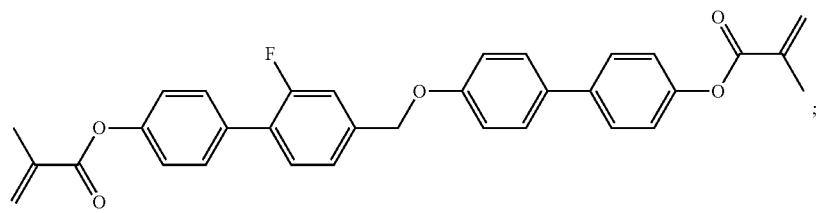
I-1-5-1
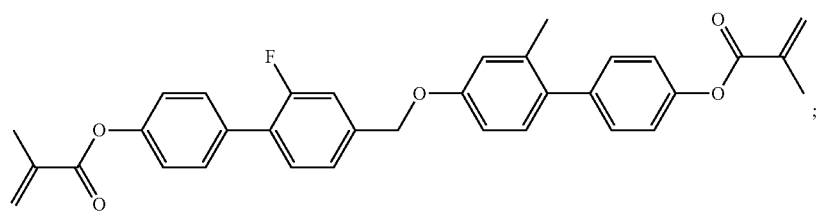
I-1-6-1
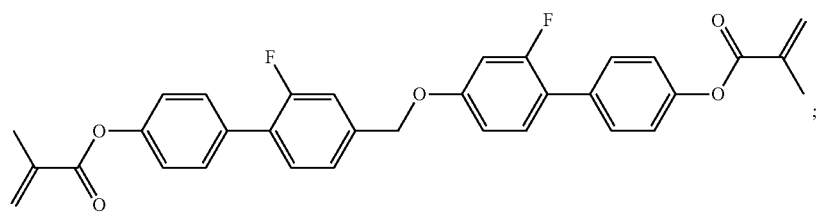
I-1-7-1
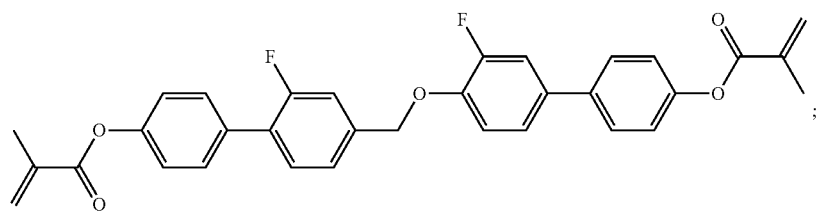
I-1-8-1
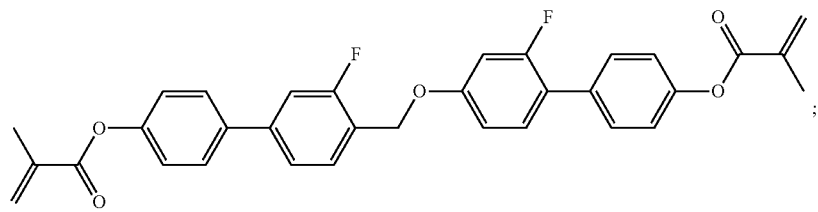

-continued
I-1-9-1
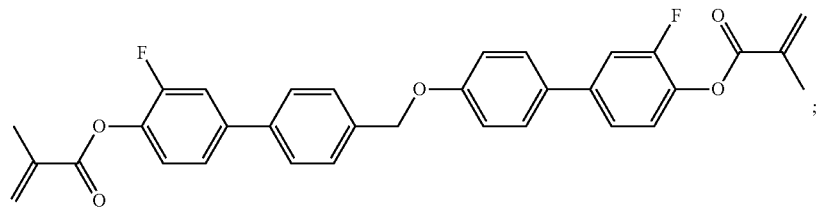
I-1-10-1
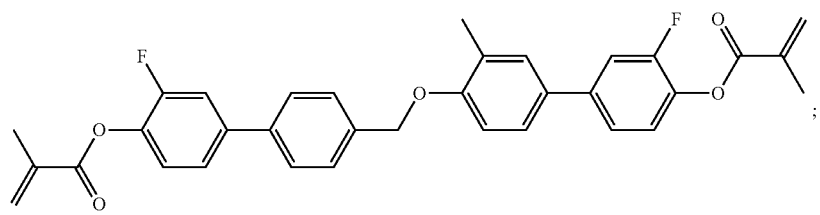
I-1-11-1
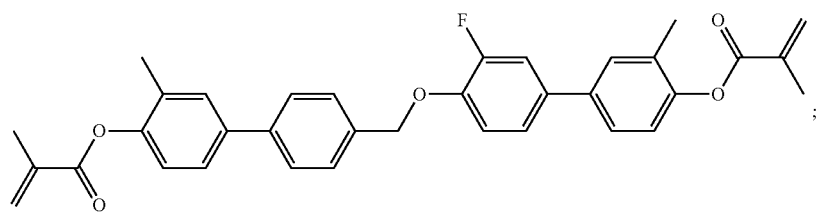
I-1-12-1
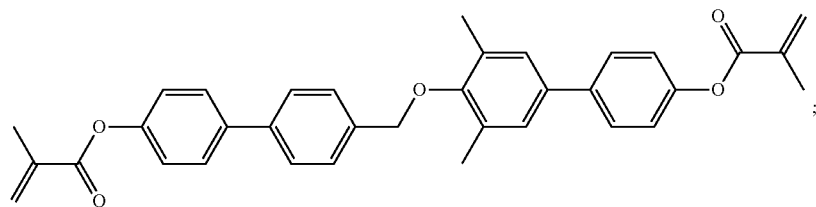
I-1-13-1
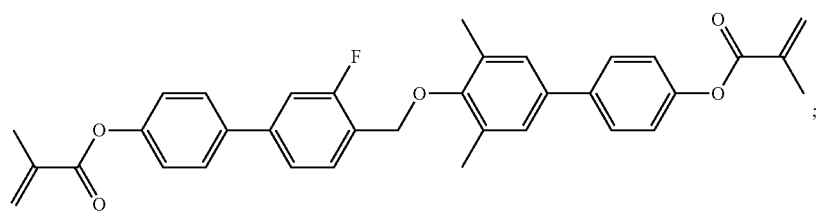
I-1-14-1
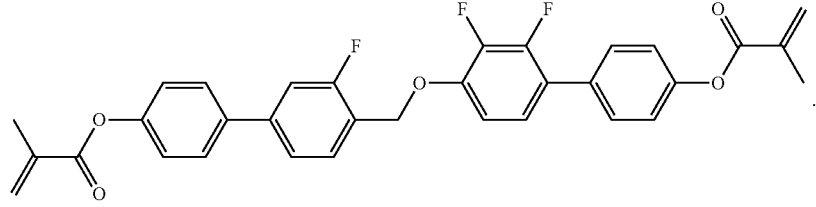

Example 2

The synthetic route of compound I-2-1-1 is shown as follows:

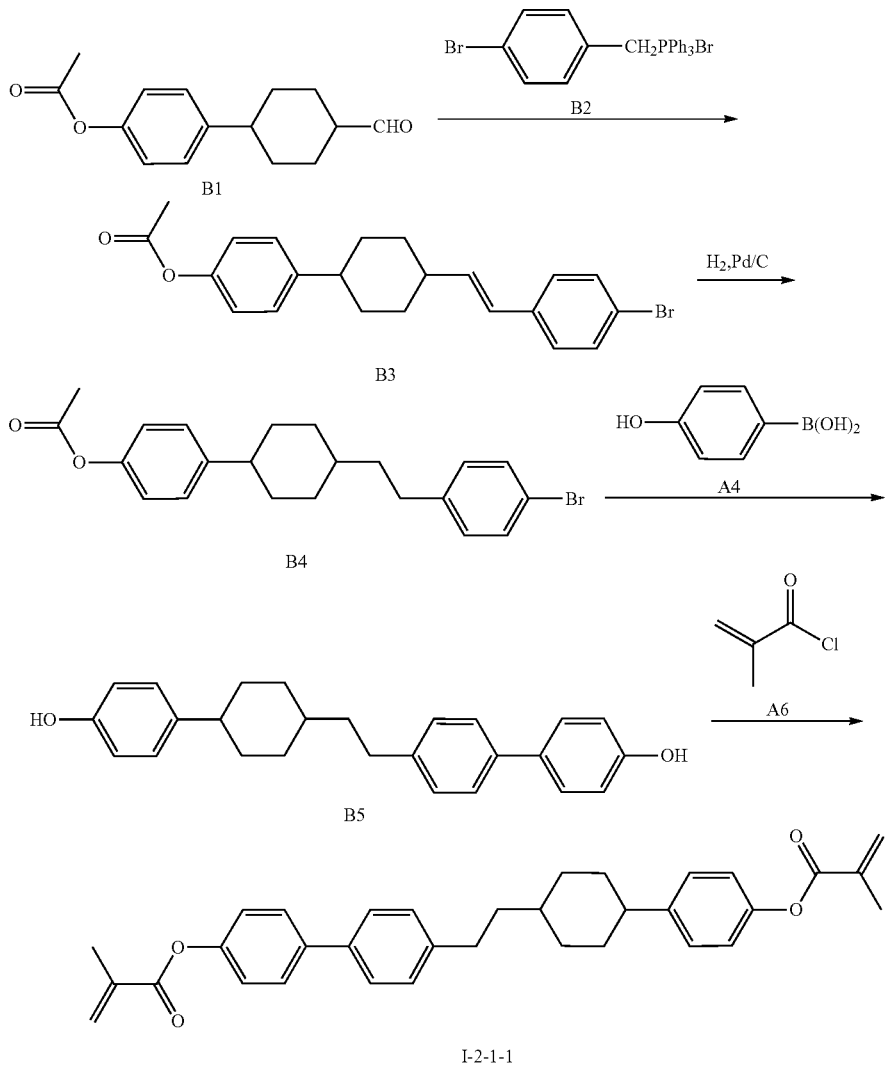

1) Synthesis of Compound B3

To a 500 ml three-necked flask was added 28.2 g B2, 250 ml anhydrous tetrahydrofuran. The temperature was cooled to 0° C. under nitrogen, and 5.6 g potassium tert-butoxide was added in portions during which the temperature was kept below 10° C. The stirring was then continued for 30 minutes, and 12.3 g of a solution of compound B1 (trans-acetoxyphenyl cyclohexylcarbaldehyde) and 50 ml anhydrous tetrahydrofuran was added dropwise. The reaction mixture was then naturally warmed to room temperature and stirred for 12 hours. After post-treatment, 13 g compound B3 was obtained, GC (containing isomers)>95%, yield: 65%.

2) Synthesis of Compound B4

To a 1 L hydrogenated kettle was added 10 g compound B3, 100 ml toluene, 100 ml ethyl acetate, and 0.5 g of 5% Pd/C. The air in the hydrogenated kettle was first discharged with nitrogen, and then the nitrogen was replaced with hydrogen. The hydrogen pressure was adjusted to 0.3 MPa, and catalytic hydrogenation was carried out at room temperature for 8 hours. After completion of the reaction and post-treatment, 10 g compound B4 was obtained, GC>95%, yield: 100%.

3) Synthesis of Compound B5

To a 500 ml three-necked flask was added 10 g compound B4, 8.5 g A4, 100 ml toluene, 50 ml ethanol, 50 ml water and 10.6 g anhydrous sodium carbonate. 0.25 g tetrakis(triphenylphosphine)palladium was added under nitrogen, and the reaction mixture was heated to reflux for 6 hours. After completion of the reaction and post-treatment, 3.6 g compound B5 was obtained, HPLC>95%, yield: 39%.

4) Synthesis of Compound I-2-1-1

To a 500 ml three-necked flask was added 3.6 g compound B5, 100 ml toluene, 50 ml triethylamine, and a trace amount of 2,6-di-tert-butyl-p-cresol. 2.5 g A6 was added dropwise under nitrogen. The reaction mixture was then kept at 40° C. and stirred for 6 hours. After post-treatment, 2.3 g compound I-2-1-1 was obtained, HPLC>99%, yield: 47%.

The mass spectrometry data of compound I-2-1-1 is as follows:

Ms: 508 (1.1%) 277 (100%) 264 (83%) 251 (34%) 200 (75%) 187 (62%) 174 (21%) 69 (36%).

According to the above synthesis methods, target compounds can be obtained by substituting the compounds shown in Table 2 for compounds B1, B2, A4 and A6:

TABLE 2

| Alternative compound of B1 | Alternative compound of B2 | Alternative compound of A4 | Alternative compound of A6 | target compound |
|---|---|---|---|---|
| | | | | I-2-2-1 |
| | | | | I-2-3-1 |
| | | | | I-2-4-1 |
| | | | | I-2-5-1 |
| | | | | I-2-6-1 |

The specific structures of the target compounds in Table 2 are shown as follows:

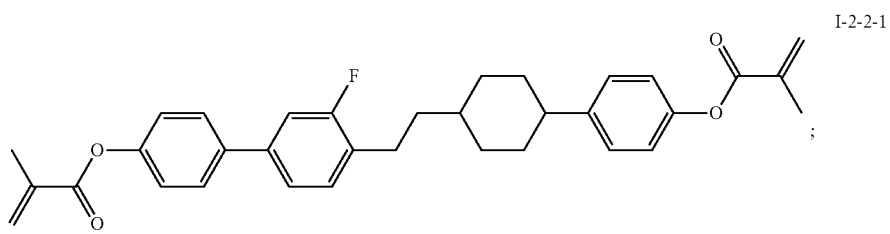

I-2-2-1

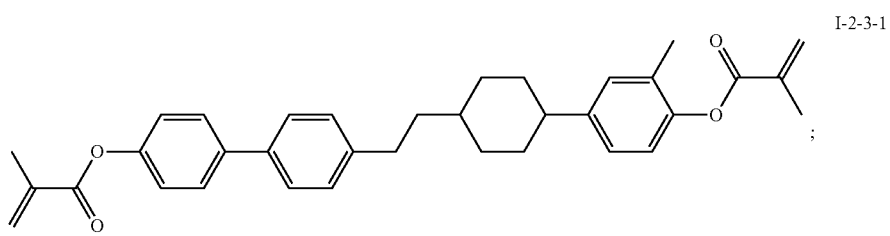

I-2-3-1

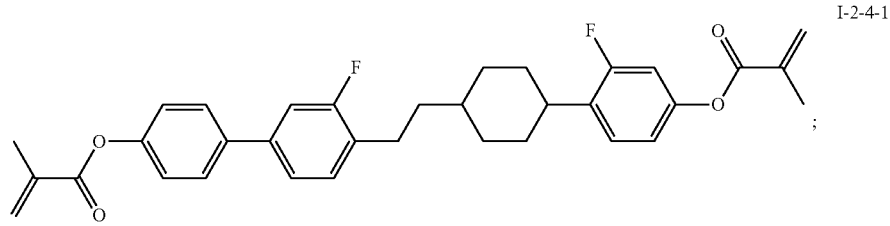
I-2-4-1
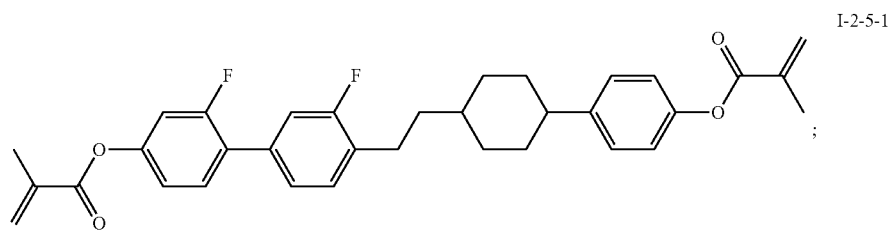
I-2-5-1
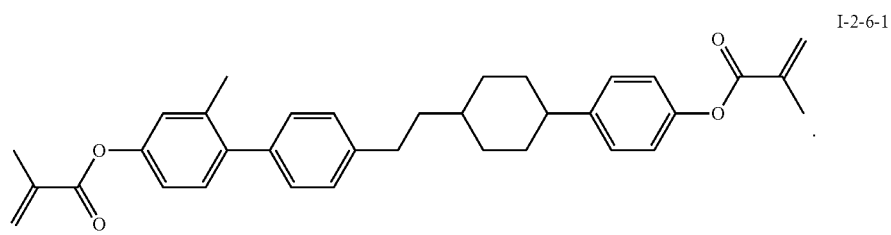
I-2-6-1
Example 3
The synthetic route of compound I-3-1-1 is shown as follows:
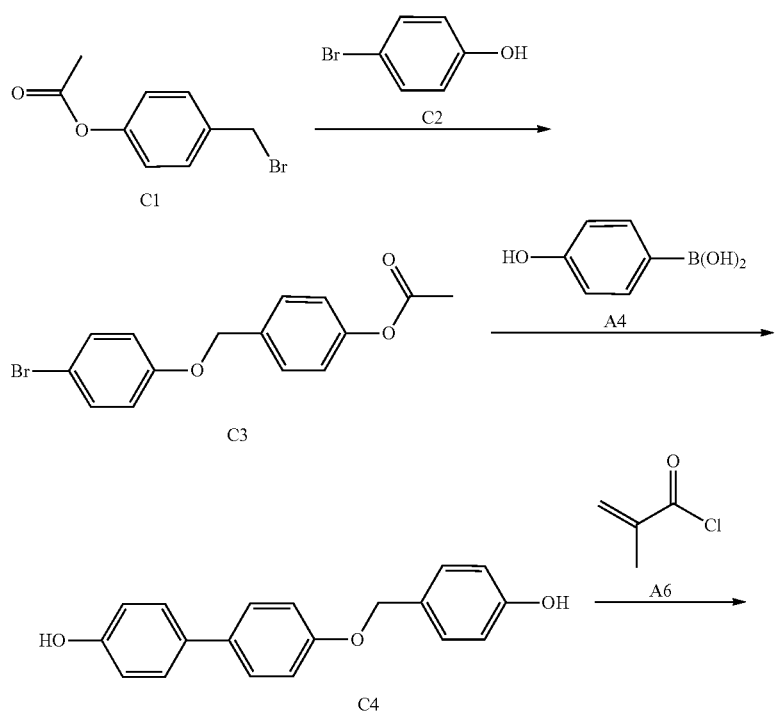

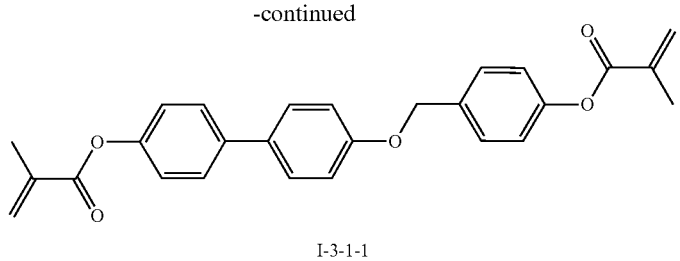

I-3-1-1

1) Synthesis of Compound C3

To a 500 ml three-necked flask was added 11.5 g C1, 8.7 g C2, 200 ml anhydrous dimethylacetamide, and 13.8 g anhydrous potassium carbonate. The reaction mixture was stirred for 3 hours at a controlled temperature of 90° C. After post-treatment, 14.5 g compound C3 was obtained, GC>97%, yield: 90%.

2) Synthesis of Compound C4

To a 500 ml three-necked flask was added 9.6 g compound C3, 4.9 g A4, 120 ml toluene, 60 ml water, 60 ml ethanol, and 12.7 g anhydrous sodium carbonate. 0.2 g tetrakis(triphenylphosphine)palladium was added under nitrogen, and the reaction mixture was heated to reflux for 6 hours. After post-treatment, 4.8 g compound C4 was obtained, GC>97%, yield: 55%.

3) Synthesis of Compound I-3-1-1

To a 500 ml three-necked flask was added 2.9 g compound C4, 100 ml toluene, 50 ml triethylamine, and a trace amount of 2,6-di-tert-butyl-p-cresol. 2.5 g A6 was added dropwise under nitrogen, and reaction mixture was stirred for 6 hours at a controlled temperature of 40° C. After post-treatment, 1.7 g compound I-3-1-1 was obtained, HPLC>99%, yield: 40%.

The mass spectrum data of compound I-3-1-1 is as follows:

Ms: 428 (3.3%) 175 (100%) 69 (49%)

According to the above synthesis methods, target compounds can be obtained by substituting the compounds shown in Table 3 for compounds C1, C2, A4 and A6:

TABLE 3

| Alternative compound of C1 | Alternative compound of C2 | Alternative compound of A4 | Alternative compound of A6 | Target compound |
|---|---|---|---|---|
| (structure) | Br—⌬—OH | HO—⌬—B(OH)₂ | (methacryloyl chloride) | I-3-2-1 |
| (structure) | Br—⌬—OH | HO—⌬—B(OH)₂ | (methacryloyl chloride) | I-3-3-1 |
| (structure) | Br—⌬—OH | HO—⌬(Me)—B(OH)₂ | (methacryloyl chloride) | I-3-4-1 |
| (structure) | Br—⌬—OH | HO—⌬(F)—B(OH)₂ | (methacryloyl chloride) | I-3-5-1 |
| (structure) | Br—⌬(F)—OH | HO—⌬—B(OH)₂ | (methacryloyl chloride) | I-3-6-1 |
| (structure) | Br—⌬(F)—OH | HO—⌬—B(OH)₂ | (methacryloyl chloride) | I-3-7-1 |

TABLE 3-continued
| Alternative compound of C1 | Alternative compound of C2 | Alternative compound of A4 | Alternative compound of A6 | Target compound |
|---|---|---|---|---|
| | | | | I-3-8-1 |
| | | | | I-3-9-1 |
| | | | | I-3-10-1 |
The specific structures of the target compounds in Table 3 are shown as follows:
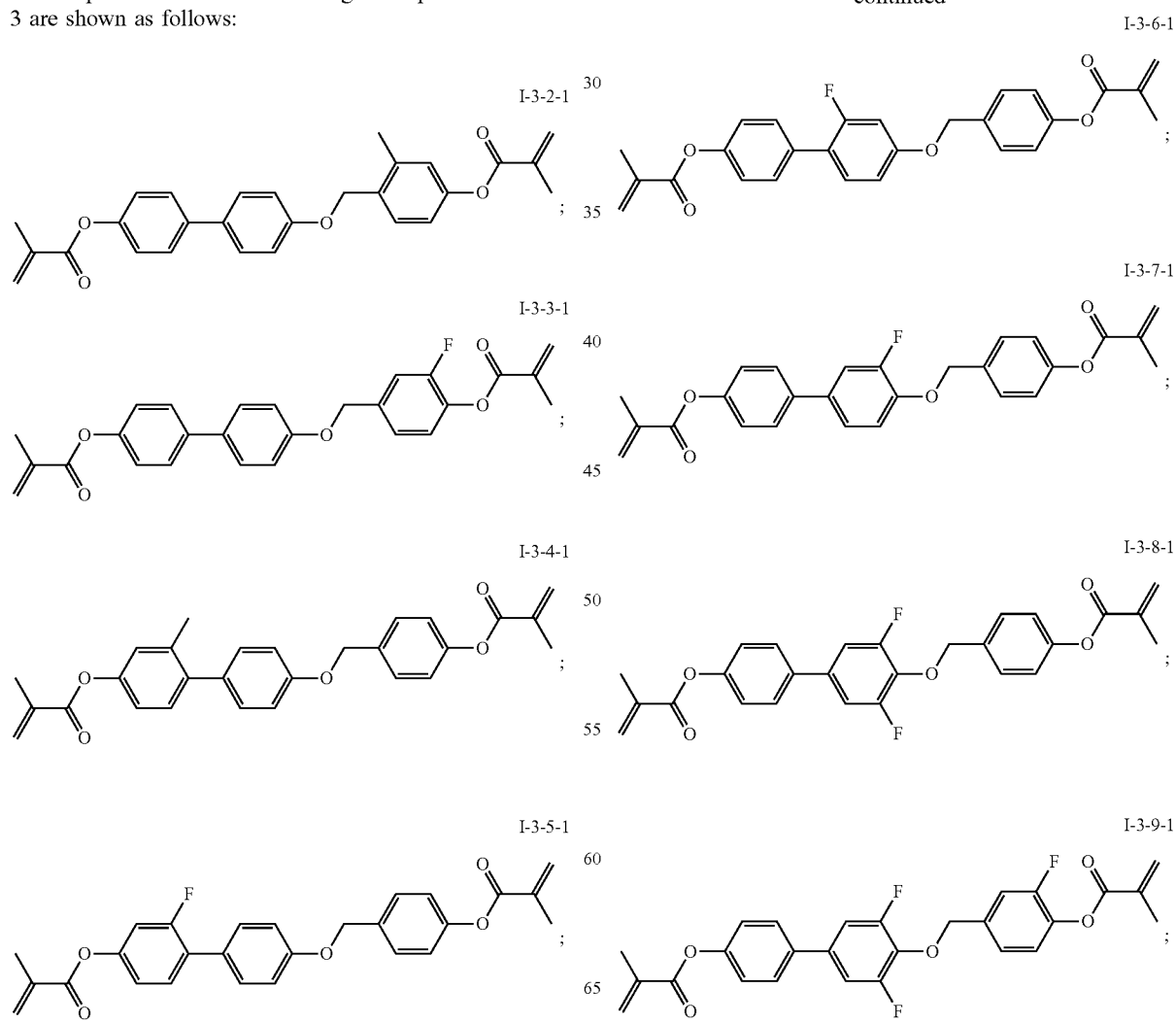

-continued

I-3-10-1

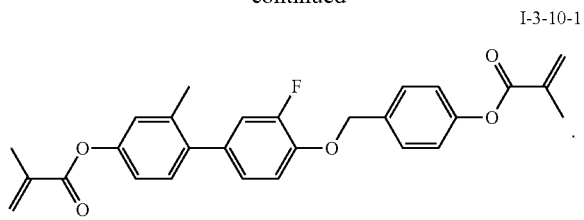

Example 4

Compounds I-1-1-1, I-1-2-1, I-1-3-1, I-1-14-1, I-2-1-1, I-2-5-1, I-3-1-1 and I-3-8-1 were added to the host liquid crystal HCMM-02 (Type: HCMM-02, Jiangsu Hecheng Display Technology Co., Ltd.) in a weight ratio of 0.3:100 of compounds to host liquid crystal respectively and heated to dissolve, thereby forming mixtures MI-1-1-1, MI-1-2-1, MI-1-3-1, MI-1-14-1, MI-2-1-1, MI-2-5-1, MI-3-1-1 and MI-3-8-1. They were naturally cooled to the laboratory ambient temperature, sampled and filled into a vertically aligned test cell to investigate the parameters of Table 4 below:

TABLE 4

|  | Dissolution | Y1(°) | VHR1(%) | VHR2(%) | Y2(°) | Y(°) |
| --- | --- | --- | --- | --- | --- | --- |
| HCMM-02 | — | 0 | 95.1 | 93.6 | 0 | 0 |
| MI-1-1-1 | No crystallization | 6.9 | 97.3 | 97.1 | 6.9 | 0 |
| MI-1-2-1 (Annotation) | Crystallization | 2.4 | 96.6 | 95.7 | 2.6 | 0.2 |
| MI-1-3-1 | No crystallization | 6.8 | 97.3 | 97 | 6.8 | 0 |
| MI-1-14-1 | No crystallization | 7.5 | 97.2 | 97.1 | 7.5 | 0 |
| MI-2-1-1 | No crystallization | 6.9 | 97.2 | 97.2 | 6.9 | 0 |
| MI-2-5-1 | No crystallization | 6.6 | 97 | 97.1 | 6.7 | 0.1 |
| MI-3-1-1 | No crystallization | 6.3 | 96.7 | 96.5 | 6.2 | −0.1 |
| MI-3-8-1 | No crystallization | 6.1 | 96.8 | 96.4 | 6.1 | 0 |

Annotation: Since there is crystallization in MI-1-2-1, the parameters in the table were obtained by testing a sample which has a weight ratio of 0.1:100 of I-1-2-1 to host liquid crystal.

It can be seen from Examples 1-4 that the polymerizable liquid crystal compositions comprising the polymerizable compounds has good stability and higher reliability, and are embodied by having a smaller pretilt angle change and higher voltage holding ratio, such that there is little or no image sticking effect in the liquid crystal display device comprising the polymerizable liquid crystal composition.

The foregoing descriptions are merely preferred examples of the present invention and are not intended to limit the present invention in any form. Although the present invention has been disclosed by the preferred examples as described above, it is not intended to be used to limit the present invention. Without departing from the scope of the technical solutions of the present invention, some changes may be made and equivalent examples can be modified through equivalent variations by those skilled in the art by means of the technical contents disclosed above. Without departing from the content of the technical solutions of the present invention, any simple amendment, equivalent change or modification of the above examples according to the technical essence of the present invention still falls within the scope of the technical solutions of the present invention.

INDUSTRIAL APPLICABILITY

The compound related in the present invention can be applied to the field of liquid crystal.

The invention claimed is:

1. A polymerizable compound comprising one or more compounds selected from compounds of general formula I-1 to I-3:

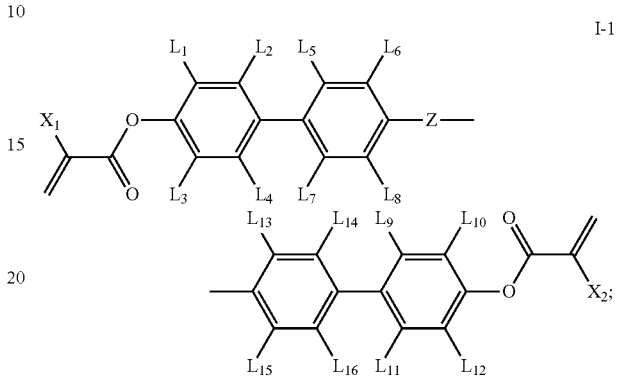

I-1

-continued

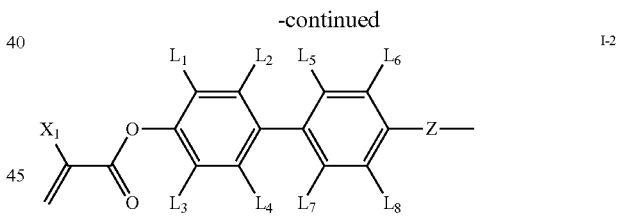

I-2

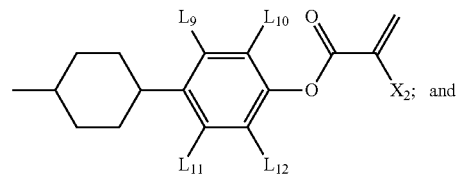

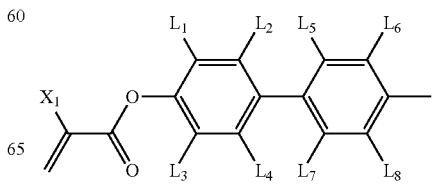

I-3

-continued

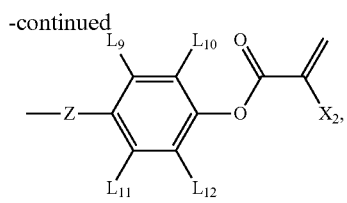

in which,

X₁ and X₂ are same or different and each independently represents —H or —CH₃;

L₁-L₁₆ are same or different and each independently represents —H, —F or —CH₃;

Z represents —CH₂O—, —OCH₂—, —CH₂CH₂—, —COO— or —OCO—;

wherein at least one of L₅-L₈ and/or L₁₃-L₁₆ in the general formula I-1 is —F or —CH₃; and wherein in general formulas I-1 and I-3 Z represents —CH₂O—, —OCH₂—, —CH₂CH₂—.

2. The polymerizable compound according to claim 1, wherein in the general formula I-2 Z represents —CH₂O—, —OCH₂— or —CH₂CH₂—.

3. The polymerizable compound according to claim 1 wherein polymerizable compound includes at least one compound represented by formula I-1, and the compound of general formula I-1 is one or more compounds selected from the following compounds:

I-1-1

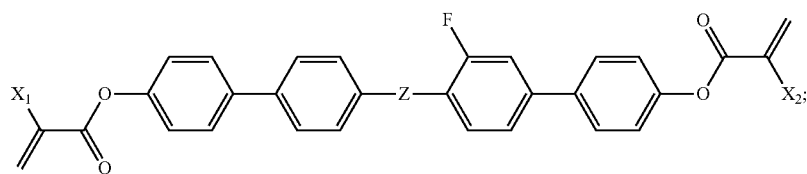

I-1-2

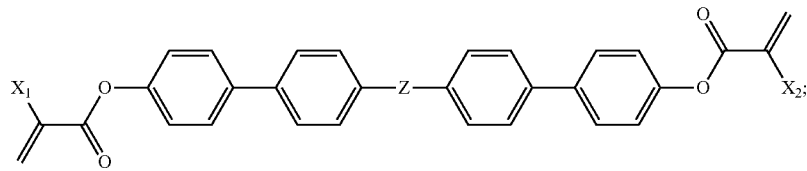

I-1-3

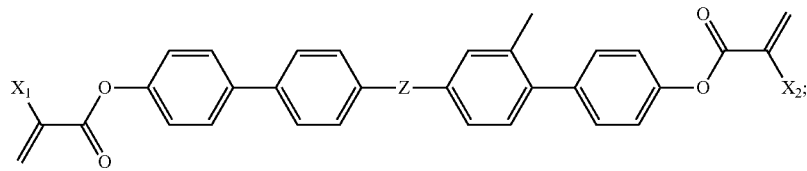

I-1-4

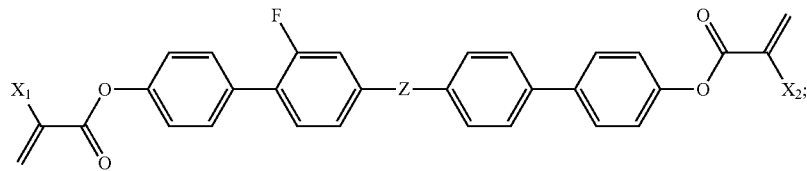

I-1-5

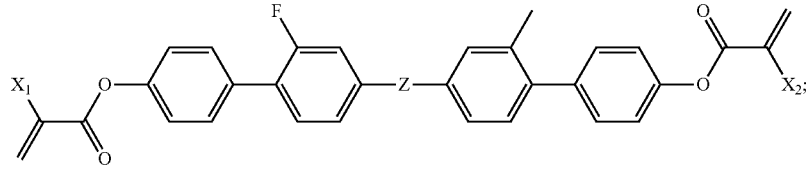

I-1-6

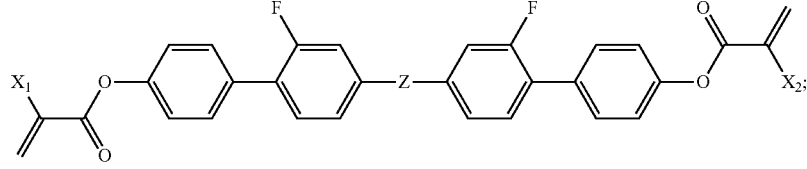

I-1-7
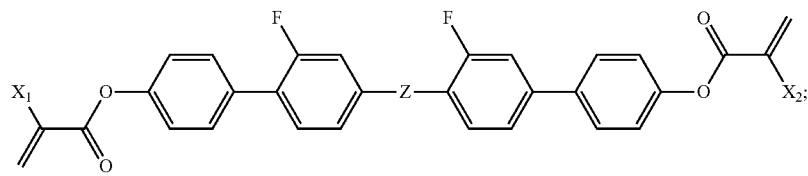
I-1-8
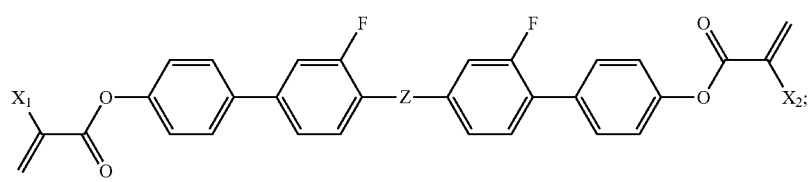
I-1-9
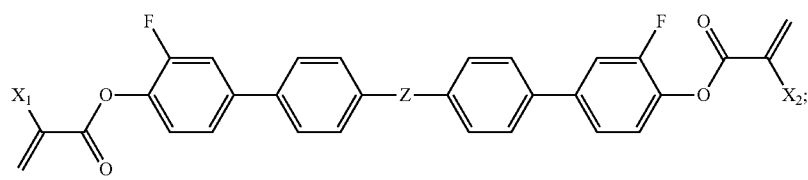
I-1-10
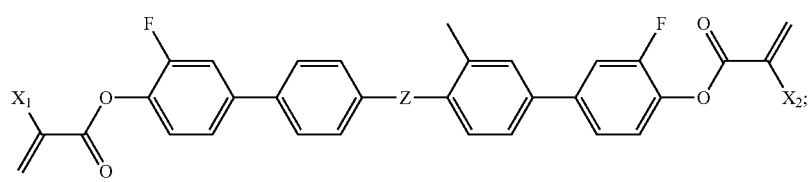
I-1-11
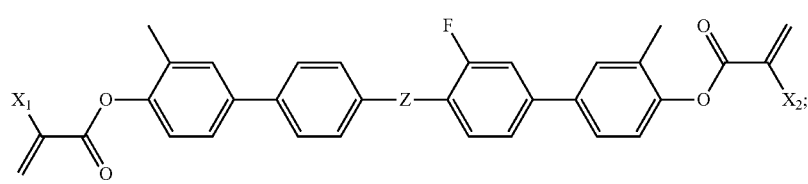
I-1-12
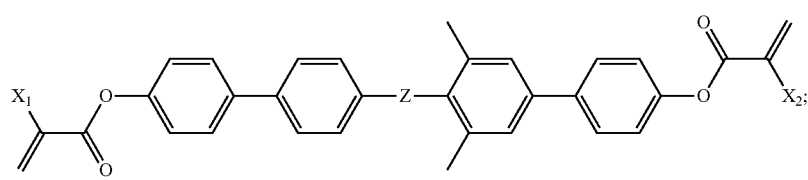
I-1-13
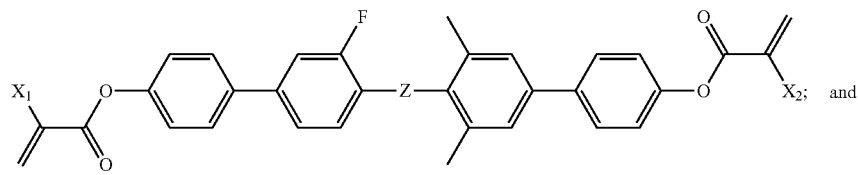 and

I-1-14

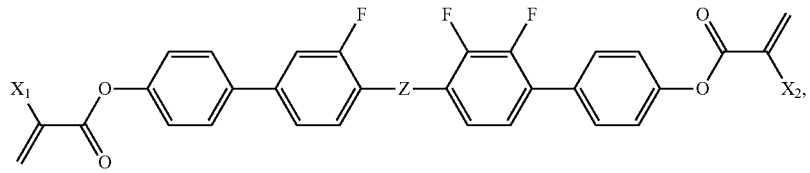

in which, $X_1$ and $X_2$ are same or different and each independently represents —H or —CH$_3$;

Z represents —CH$_2$O—, —OCH$_2$— or —CH$_2$CH$_2$—.

4. The polymerizable compound according to claim 1 wherein polymerizable compound includes at least one compound represented by formula I-2, and the compound of general formula I-2 is one or more compounds selected form the following compounds:

I-2-1
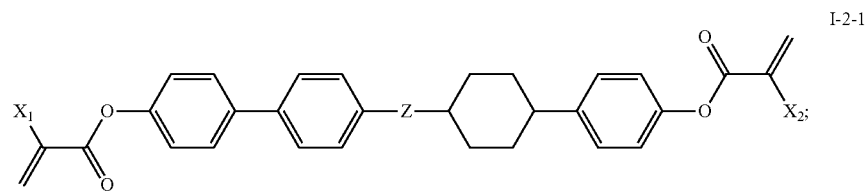

I-2-2
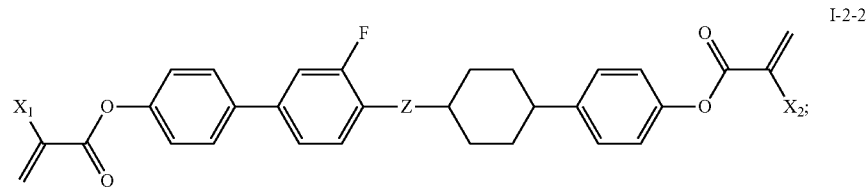

I-2-3
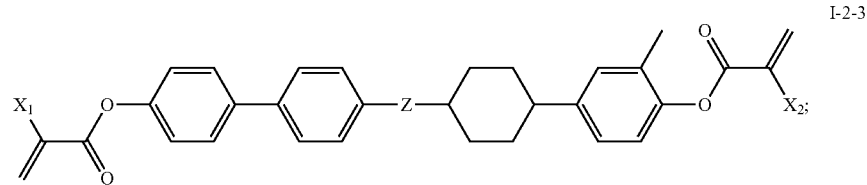

I-2-4
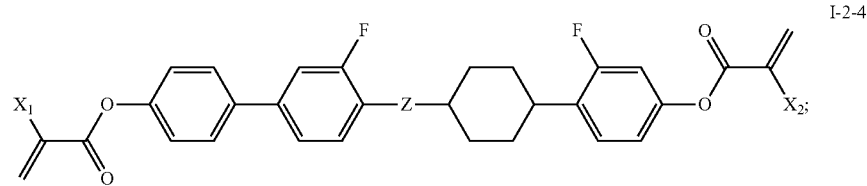

I-2-5
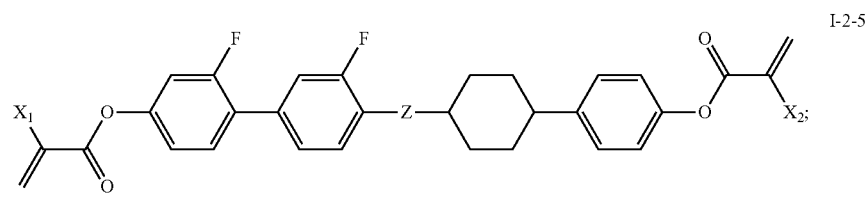

I-2-6
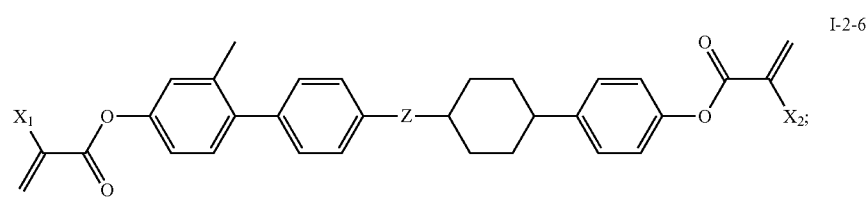

in which,

X$_1$ and X$_2$ are same or different and each independently represents —H or —CH$_3$, and Z represents —CH$_2$O—, —OCH$_2$—, —CH$_2$CH$_2$—, —COO—, or —OCO—.

5. The polymerizable compound according to claim 1 wherein polymerizable compound includes at least one compound represented by formula I-3, and the compound of general formula I-3 is one or more compounds selected form the following compounds:

I-3-1
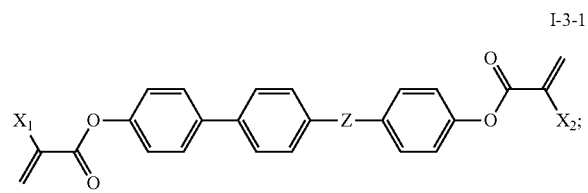

I-3-2
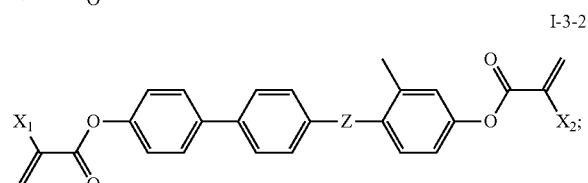

I-3-3
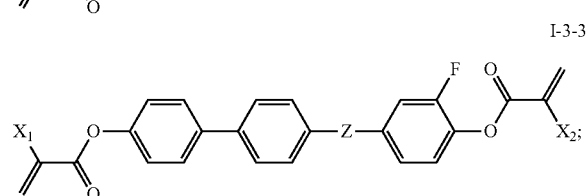

I-3-4
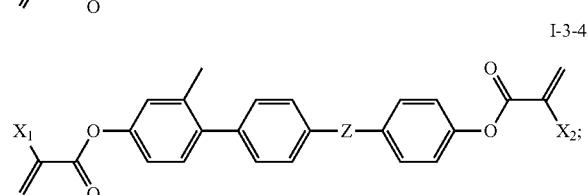

I-3-5
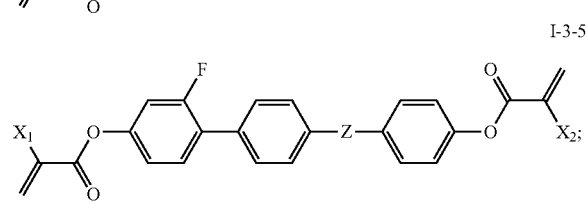

-continued

I-3-6
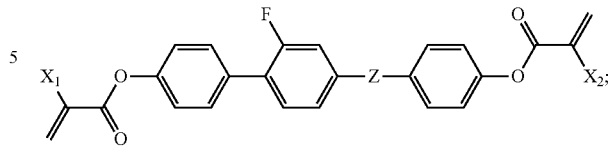

I-3-7
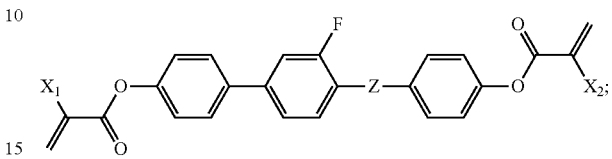

I-3-8
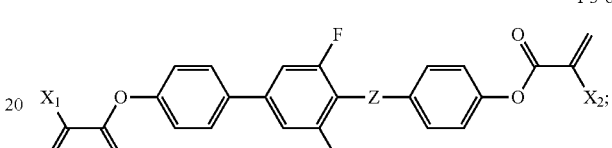

I-3-9
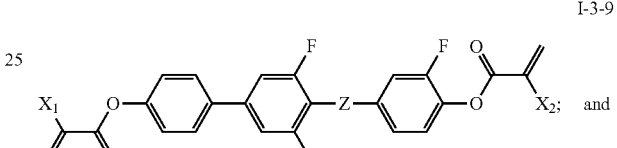

and

I-3-10
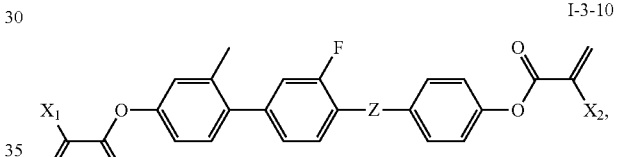

in which,

X$_1$ and X$_2$ are same or different and each independently represents —H or —CH$_3$;

Z represents —CH$_2$O—, —OCH$_2$— or —CH$_2$CH$_2$—.

6. A polymerizable liquid crystal composition comprising the polymerizable compound of claim 1.

7. A liquid crystal display device comprising the polymerizable liquid crystal composition of claim 6.

8. A polymerizable compound comprising one or more compounds selected form the following compounds:

I-2-1
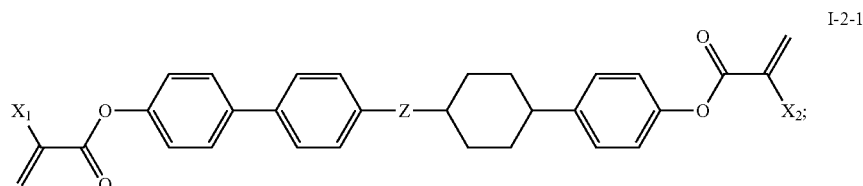

I-2-2
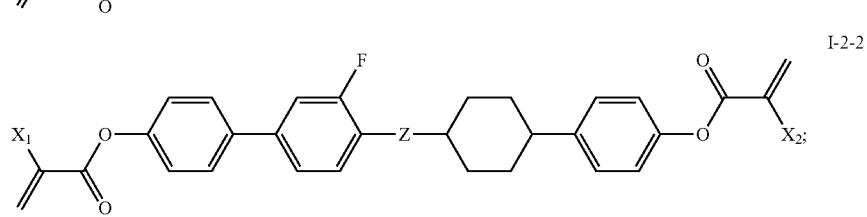

-continued
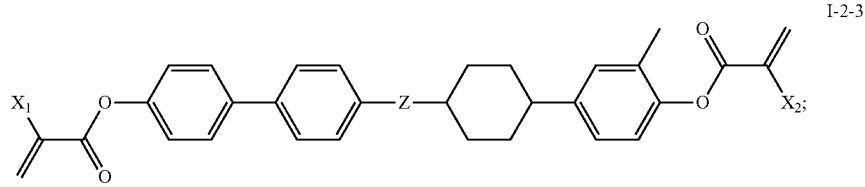
I-2-3
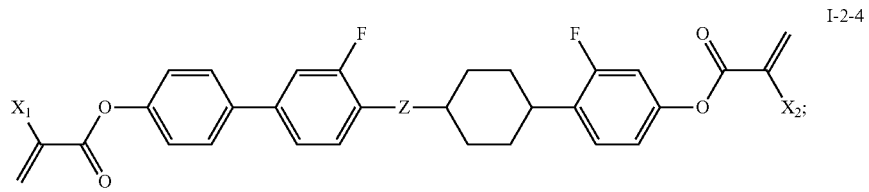
I-2-4
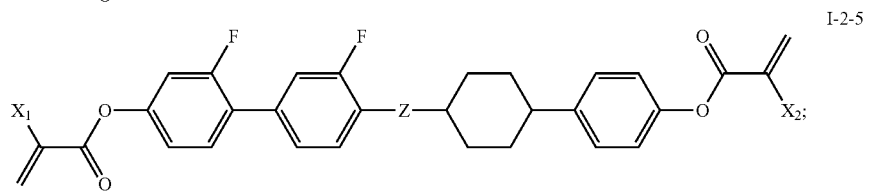
I-2-5
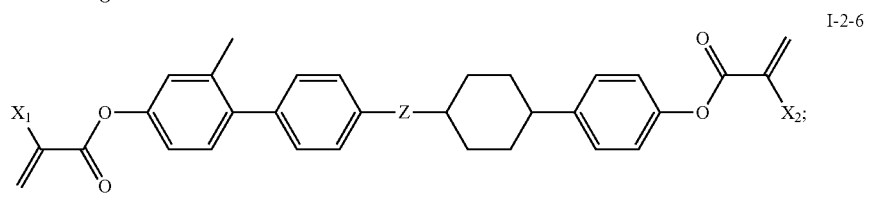
I-2-6
in which,
X₁ and X₂ are same or different and each independently represents —H or —CH₃, and
Z represents —CH₂O—, —OCH₂—, —CH₂CH₂—, —COO—, —OCO—, —CF₂O— or —OCF₂—.
9. A polymerizable compound comprising one or more compounds selected from the following compounds:
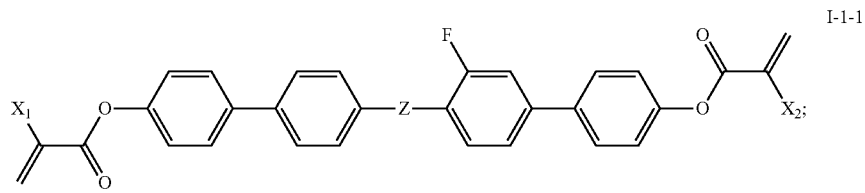
I-1-1
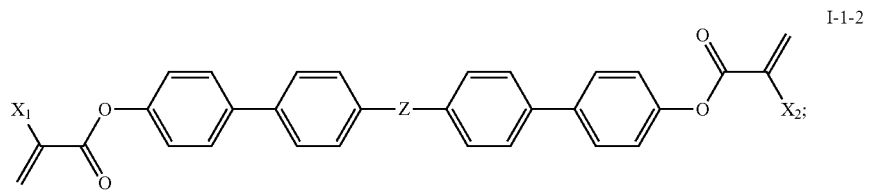
I-1-2
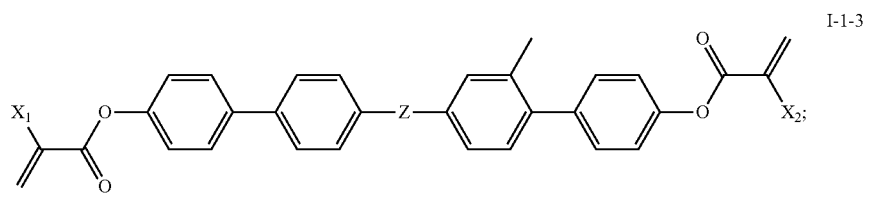
I-1-3

-continued
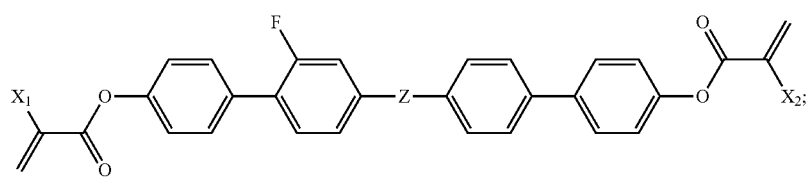
I-1-4
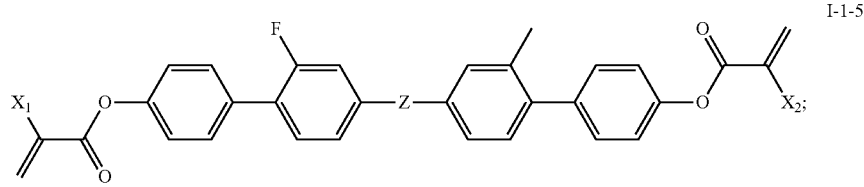
I-1-5
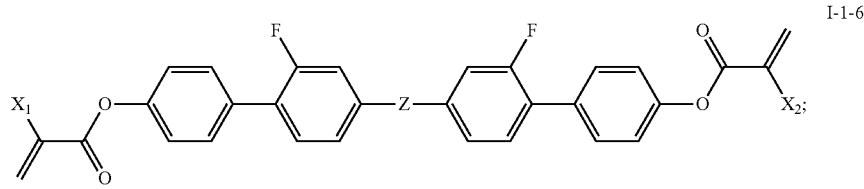
I-1-6
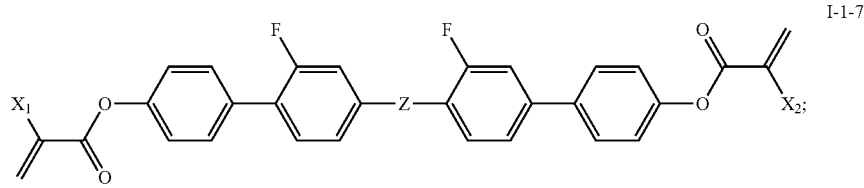
I-1-7
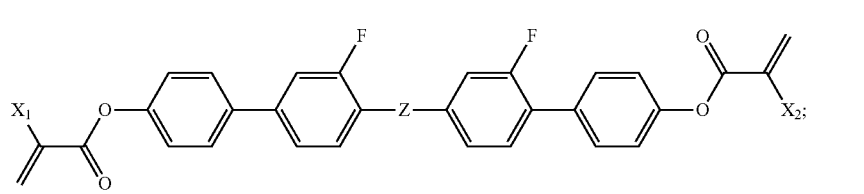
I-1-8
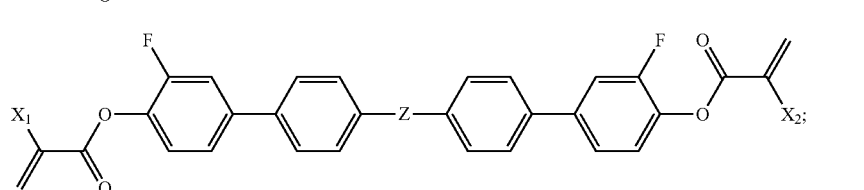
I-1-9
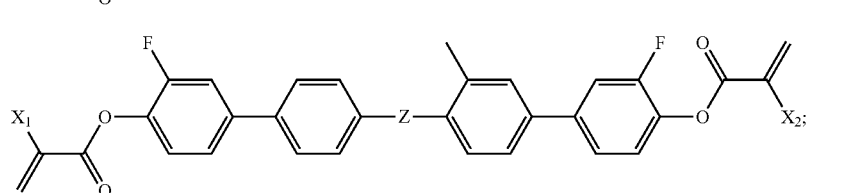
I-1-10
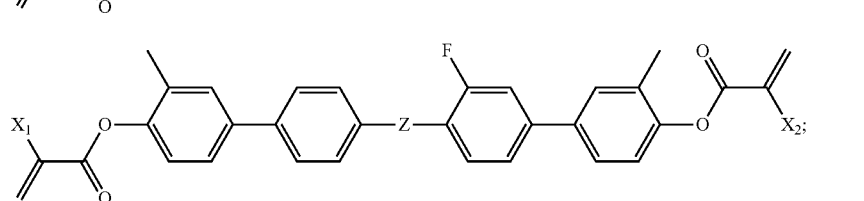
I-1-11
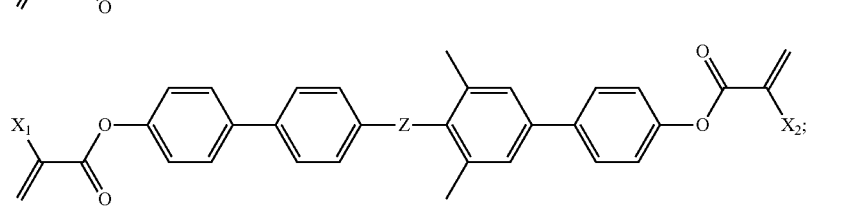
I-1-12

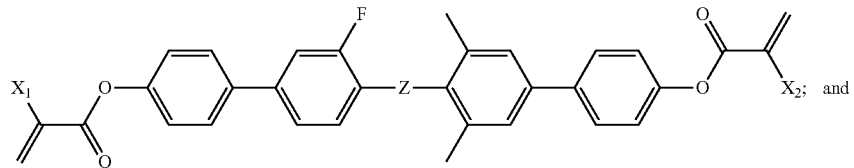
I-1-13
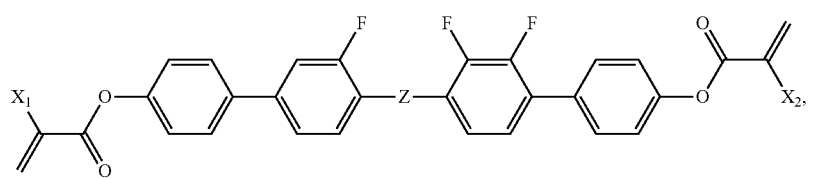
I-1-14
in which,
$X_1$ and $X_2$ are same or different and each independently represents —H or —$CH_3$;
Z represents —$CH_2O$—, —$OCH_2$— or —$CH_2CH_2$—.